(12) United States Patent
Detmer et al.

(10) Patent No.: US 7,993,838 B2
(45) Date of Patent: Aug. 9, 2011

(54) NUCLEIC ACID PRIMERS AND PROBES FOR DETECTING HUMAN AND AVIAN INFLUENZA VIRUSES

(75) Inventors: Jill Detmer, Kensington, CA (US); Charlene Bush-Donovan, Livermore, CA (US)

(73) Assignee: Siemens Healthcare Diagnostics Inc., Tarrytown, NY (US)

( * ) Notice: Subject to any disclaimer, the term of this patent is extended or adjusted under 35 U.S.C. 154(b) by 334 days.

(21) Appl. No.: 12/298,607

(22) PCT Filed: Apr. 20, 2007

(86) PCT No.: PCT/US2007/067153
§ 371 (c)(1),
(2), (4) Date: Oct. 27, 2008

(87) PCT Pub. No.: WO2008/140513
PCT Pub. Date: Nov. 20, 2008

(65) Prior Publication Data
US 2010/0330548 A1    Dec. 30, 2010

Related U.S. Application Data

(60) Provisional application No. 60/795,785, filed on Apr. 28, 2006.

(51) Int. Cl.
*C12Q 1/68* (2006.01)
(52) U.S. Cl. .......................................................... 435/6
(58) Field of Classification Search .................. None
See application file for complete search history.

(56) References Cited

U.S. PATENT DOCUMENTS
6,015,664 A * 1/2000 Henrickson et al. .............. 435/5

FOREIGN PATENT DOCUMENTS
WO    2004057021    7/2004
WO    2005121367    12/2005
WO    2006000140    1/2006

OTHER PUBLICATIONS

Spackman et al. (J Clin Microbiol. Sep. 2002;40(9):3256-60).*
van Elden et al. (J Clin Microbiol. Jan. 2001;39(1):196-200).*
NBCI (GENBANK Accession No. AB027409; Mar. 6, 2003).*
Buck et al ("Design Strategies and Performance of Custom DNA Sequencing Primers" Biotechniques. 1999. 27(3): pp. 528-536).*
Lowe et al. (Nucleic Acids Research, vol. 18, No. 7, p. 1757-1761, 1990).*
Starick et al., Type- and subtype-specific RT-PCR assays for avian influenza A viruses (AIV), J. Vet. Med. B Infect. Dis. Vet. Public Health, 47(4):295-301 (2000).
Munch et al., Detection and subtyping (H5 and H7) of avian type A influenza virus by reverse transcription-PCR and PCR-ELISA, Arch Virol., 146(1): 87-97 (2001).
Spackman et al., Development of a real-time reverse transcriptase PCR assay for type A influenza virus and the avian H5 and H7 hemagglutinin subtypes, J. Clin. Microbiol., 40(9): 3256-60 (2002).
Dybkaer et al., Application and evlaution of RT-PCR-ELISA for the nucleoprotein and RT-PCR for detection of low-pathogenic H5 and H7 subtypes of avian influenza virus, J. Vet. Diang. Invest., 16(1) 51-6 (2004).
Payungporn et al., Single-step multiplex reverse transcription-polymerase chain reaction (RT-PCR for influenza A virus subtype H5N1 detection, Viral Immunol. 17(4):588-93 (2004).

* cited by examiner

*Primary Examiner* — Christopher M. Babic

(57) ABSTRACT

Provided are nucleic acid sequences that are used to prepare primers and probes that are used in a kinetic polymerase chain reaction (kPCR) assay to detect influenza viruses in a human or animal subject. The starting material for the kPCR assays may be DNA or RNA and the assays may be conducted in a singleplex assay to detect a single influenza virus or in a multiplex assay to detect multiple influenza viruses. The primers and probes have utility in the detection and quantification of type A and type B influenza viruses (INFA and INFB, respectively) and have been shown to be effective for the detection and quantification of all the known INFA subtypes, namely, H1, H2, H3, H4, H5, H6, H7, H8, and H9.

18 Claims, 4 Drawing Sheets

NUCLEIC ACID PRIMERS AND PROBES FOR DETECTING HUMAN AND AVIAN INFLUENZA VIRUSES

CROSS-REFERENCE TO RELATED APPLICATION

This application claims priority under 35 U.S.C. §119(e) to U.S. Provisional Patent Application No. 60/795,785, filed on Apr. 28, 2006, the disclosure of which is incorporated herein in its entirety.

TECHNICAL FIELD

The present invention relates generally to nucleic acid sequences useful for diagnostic assay for the detection of human and avian influenza viruses. More specifically, the present invention relates to primers and probes specific for detecting subtypes of the avian influenza A ("INFA") virus and strains of the human INFA and influenza B ("INFB") viruses. The sequences may be used in a singleplex assay to detect the influenza viruses in a sample or they may be used in multiplex assays to detect the influenza viruses along with other respiratory diseases in a sample.

BACKGROUND OF THE INVENTION

There are three types of influenza viruses: INFA, INFB, and influenza C ("INFC"). The most virulent influenza virus is influenza virus A, which can infect humans, birds, pigs, horses, seals, whales, and other animals. Influenza viruses that use wild birds as natural hosts are referred to as avian influenza viruses and influenza viruses that use humans as natural hosts are referred to as human influenza viruses. Domesticated birds, such as turkeys and chickens, have developed fatal illnesses from avian influenza virus, as have other animals and humans that have become infected with avian influenza virus through contact with infected domesticated birds. Domesticated birds may become infected with avian influenza virus through direct contact with infected wild birds, other infected animals, contact with surfaces harboring viruses, or contaminated food or water. Thus far, avian influenza viruses that have crossed species and infected humans are responsible for recent human influenza pandemics. The influenza B and influenza C viruses, both of which normally only infect humans, are less virulent than influenza A. While influenza B has been responsible for localized epidemics of influenza, it has not been the cause of any widespread influenza pandemics. The least virulent influenza C virus has never led to any widespread human influenza epidemics.

The influenza virus is an enveloped virus with a genome containing eight single-stranded negative sense RNA segments. The viral envelope has a host-derived lipid bilayer with two major surface viral glycoproteins: hemagglutinin ("HA") and neuraminidase ("NA"), which are the proteins responsible for viral attachment. Within the envelope, matrix protein M1 and nucleoprotein ("NP") protect the viral RNA. The A, B, and C type designation of the influenza virus is based upon the antigenic features of the M1 matrix protein and NP. The eight RNA segments encode at least 10 viral proteins: segments 1, 2, and 3 encode three viral polymerase proteins; segment 4 encodes HA; segment 5 encodes NP; segment 6 encodes NA; segment 7 encodes the M1 and M2 matrix proteins, the former which has ion channel activity and is embedded in the viral envelope; and segment 8 encodes the nonstructural proteins NS1 and NS2, the former which blocks the hosts antiviral response and the latter which participates in the assembly of virus particles.

INFA viruses are identified by the subtype of the HA and NA proteins on the surface of the virus. INFA viruses have 16 different HA subtypes and 9 different NA subtypes, all of which may exist on the surface of the virus in many different combinations; thus, an H5N1 virus has an HA5 protein and an NA1 protein on its surface. All subtypes of INFA viruses are found in birds. The INFA subtypes commonly found in humans are the H1, H2, and H3 subtypes (H2 subtypes are currently not circulating) with the H5, H7, and H9 subtypes also having been known to infect humans. Among the INFA viruses found in birds, the H5 and H7 subtypes are the most virulent; strains of the H5 and H7 subtypes are further classified as either low pathogenic avian influenza ("LPAI") or high pathogenic avian influenza ("HPAI"). HPAI are characterized by HAs that are highly susceptible to cleavage by numerous cellular proteases, which are widespread in cell compartments and organ systems; by contrast, LPAIs require specific active extra-cellular proteases, such as trypsin, which are restricted to the lumen of the respiratory and intestinal sites, for cleavage. Of domesticated birds infected with HPAI H5 or H7 viruses, 90% to 100% of the birds will die. Because LPAI H5 and H7 viruses can evolve into HPAI H5 and H7 viruses, respectively, outbreaks of LPAI H5 and H7 viruses in domesticated bird populations must be closely monitored. Subtypes of avian influenza virus circulating among animals and humans include the H7N7 and H3N8 viruses, which cause illness in horses, and the H1N1, H1N2, and H3N2 viruses, which are in general circulation among humans. INFB and INFC viruses are not classified according to subtype.

Since 1997, INFA viruses previously exclusive to infection in birds have been infecting humans with fatal outcomes. Confirmed outbreaks of avian influenza virus with some resultant human deaths have been reported in 1997 (H5N1 in Hong Kong), 1999 (H9N2 in China and Hong Kong), 2002 (H7N2 in Virginia, USA), 2003 (H5N1 in China and Hong Kong; H7N7 in the Netherlands; H9N2 in Hong Kong; H7N2 in New York, USA); 2004 (H5N1 in Thailand and Vietnam; H7N3 in Canada); and 2005 (H5N1 in Thailand and Vietnam).

Because avian IFNA viruses are carried globally via migratory birds and the virus is known to change rapidly as a result of antigenic drift and shirt and genetic drift, methods used for surveillance of avian influenza virus must have sufficient specificity to allow detection of antigenically and genetically diverse influenza strains.

Traditional methods to detect avian INFA include plaque assays, such as Culture Enhanced Enzyme Linked Immunosorbent Assay ("CE-ELISA") and virus isolation in embryonated chicken eggs. Hemagglutinin and neuraminidase subtyping of the virus is carried out after detection by serological methods. While the traditional methods have been shown to be sufficiently sensitive, the processes are time-consuming; for example, virus isolation in embryonated eggs takes from one to two weeks to obtain results.

To overcome the time and cost disadvantages of the traditional methods of detecting avian INFA, diagnostic methods using the technique known as real time reverse transcriptase polymerase chain reaction ("real time RT-PCR"), also called kinetic RT-PCR ("kRT-PCR"), have been developed. Such assays detect INFA and INFB using sequences derived from the INFA and INFB matrix and nucleoprotein genes. Stone et al., J. VIROL. METH. 117:103-112 (2003); Smith et al., J. CLIN. VIR. 28:51-58 (2003); Ward et al., J. CLIN. VIR. 29:179-188 (2004). For those assays that have been directed to the INFA H5 and H7 HA subtypes, the results of the assays were not found to be superior over traditional serotyping for HA subtypes. Spackman et al., J. CLIN. MICROBIOL. 40(9):3256-3260 (2002); Munch et al., ARCH. VIROL. 146:87-97 (2001); Lee & Suarez, J. VIROL. METH. 119:151-158 (2004).

In order to be able to detect and treat INFA and IFNB viruses in humans and animals, there remains a need in the art for highly sensitive assays that are capable of detecting all INFA and INFB strains and subtypes.

SUMMARY OF THE INVENTION

The present invention overcomes the need in the art for a highly sensitive assay that is capable of detecting all INFA and INFB strains and subtypes in a human or animal subject by providing sets of amplification primers and detection probes designed to be inclusive of all strains of INFA and IFNB as well as all subtypes of INFA. For the detection of avian INFA, the primer and probe sets of the present invention detect nucleic acid sequences of the H5 subtype of the HA gene that are conserved among various avian species (Table 1). For the detection of human INFA, the primer and probe sets of the present invention detect nucleic acid sequences of the matrix (M1) genes that are conserved among multiple human samples (Table 2). For the detection of human INFB, the primer and probe sets of the present invention detect nucleic acid sequences of the nonstructural (NS1 and NS2) genes that are conserved among multiple human samples (Table 3). Because the methods described herein may be used to develop primers and probes that detect conserved nucleic acid sequences for any genes expressed in any of the segments of the influenza virus (for any species), it is understood that the method of the present invention is not limited to the avian and human primer and probe sets described herein.

In one embodiment of the present invention, there is provided a method of detecting and quantifying influenza viruses in a sample comprising conducting a kinetic polymerase chain reaction assay performed with primers and probes prepared from SEQ ID NOs. 1-11.

In another embodiment of the invention, the influenza virus is avian influenza virus A (INFA) and the primers and probes are prepared from SEQ ID NOs. 1-5 to detect and quantify both lineages of subtype H5 of avian INFA. There are two lineages of avian influenza A/H5 viruses: the Eurasian and American lineages. Viruses from these two lineages are genetically different. All known human influenza H5 infections have been causes by highly pathogenic viruses from the Eurasian lineage.

In a further embodiment of the invention, the influenza virus is human influenza virus A (INFA) and the primers and probes are prepared from SEQ ID NOs. 6-8 to detect and quantify matrix genes of human INFA, and In yet another embodiment of the invention, the influenza virus is human influenza virus B (INFB) and the primers and probes are prepared from SEQ ID NOs. 9-11 to detect and quantify nonstructural genes of human INFB.

In still a further embodiment of the invention, the primers and probes are used in a kinetic polymerase chain reaction assay ("kPCR") to detect and quantify the influenza viruses. For the kPCR assay, the sample may be a DNA sample obtained from a human or animal subject or an RNA sample obtained form a human or animal subject. Where the starting sample is RNA, the kPCR assay is a kinetic reverse transcriptase PCR (kRT-PCR) assay.

Additional aspects, advantages, and features of the invention will be set forth, in part, in the description that follows, and, in part, will become apparent to those skilled in the art upon examination of the following or upon practice of the invention.

DETAILED DESCRIPTION OF THE INVENTION

Definitions

The definitions provided below are set forth only to assist in the comprehension of the invention as disclosed and claimed; the definitions and nomenclature are not intended to be limiting.

As used in this specification and the appended claims, the singular forms "a," "an," and "the" include plural referents unless the context clearly dictates otherwise.

As used herein, the term "epidemic" refers to an outbreak of influenza that spreads rapidly and affects many individuals in an area or a population at the same time.

As used herein, the term "pandemic" refers to an epidemic of influenza that spreads over a wide geographic area and affects a large proportion of the population.

The term "antigenic drift" refers to small changes in a virus that occur continually over time. With in the context of the influenza virus, antigenic drift produces new avian influenza virus strain that may not be recognized by antibodies to earlier influenza strains. Antigenic drift is a common occurrence of avian influenza virus.

The term "antigenic shift" refers to an abrupt, major change in a virus that produces a new virus. Within the context of the influenza virus, antigenic shift results in a new influenza virus subtype. Unlike antigenic drift, antigenic shift occurs infrequently.

The term "genetic drift" refers to random fluctuations in the frequency of the appearance of a gene in a small isolated population that is not the result of natural selection.

The term "mutation" refers to any change in the sequence of genomic DNA.

The term "homology" refers to a genetic relationship resulting from a unique inheritable modification of a feature at some previous point in time. The term is used to refer to DNA, genes, or other characters deriving from a common ancestor, having the same origin.

The term "conserved" is used to refer to a similarity in sequence, structure, or function.

The term "alignment" refers to any series of techniques for juxtaposing homologous molecular sequences for phylogenetic analyses.

Figure 1:
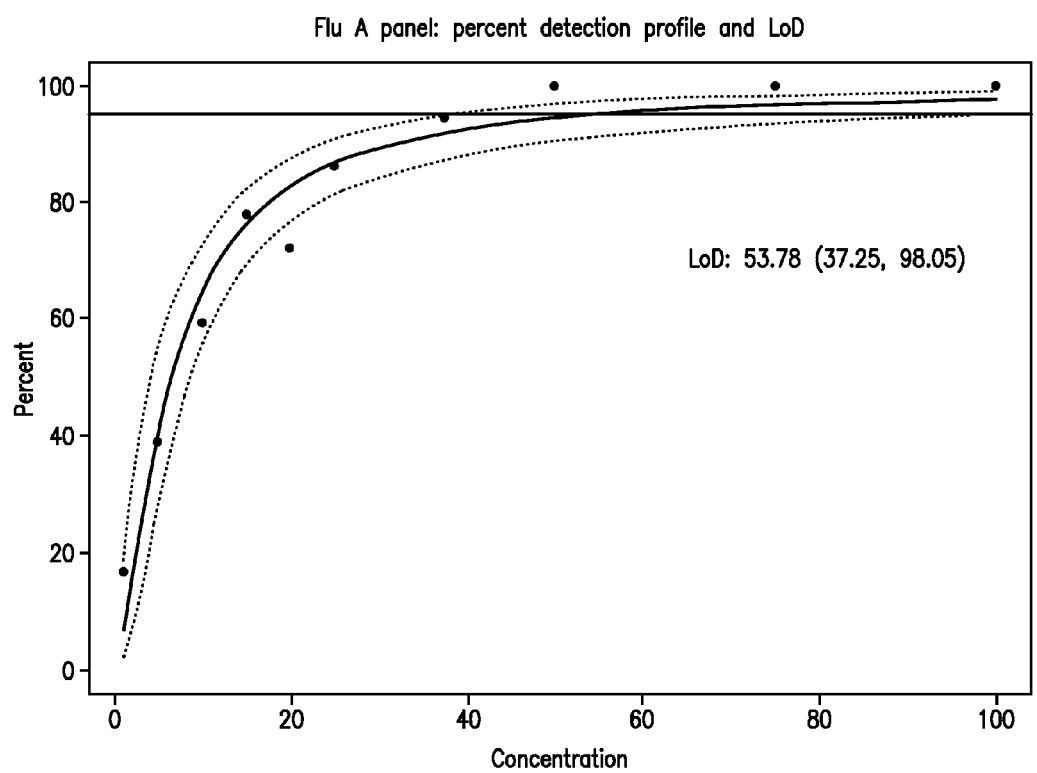
FIG. 1 shows the detection profile for the INFA matrix assay of the present invention.
Figure 2A:
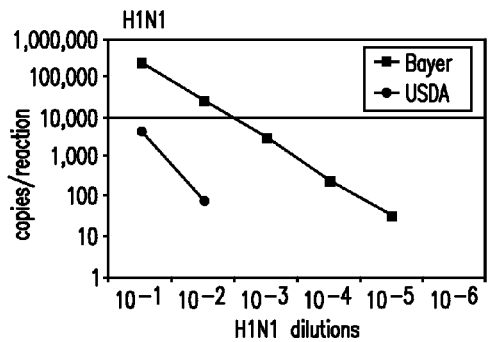
FIGS. 2(*a*) to (*h*) show the results of a comparative analysis of the same avian viral stocks screened for a panel of INFA subtypes using the pan-INFA matrix assay of the present invention and the pan-INFA matrix assay used by the USDA-ARS.
Figure 2B:
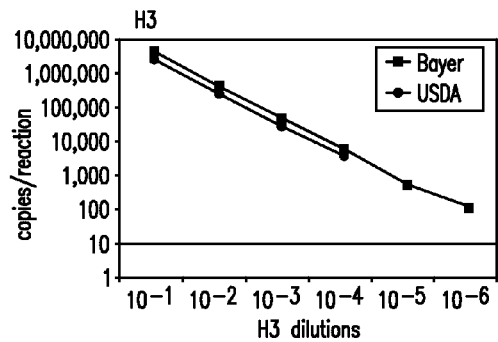
Figure 2C:
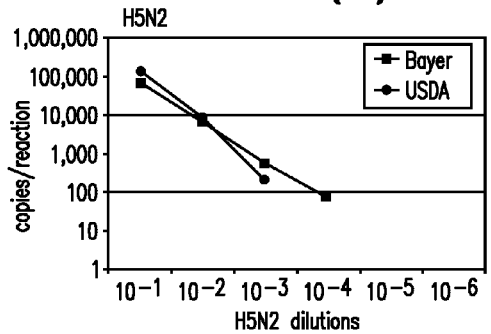
Figure 2D:
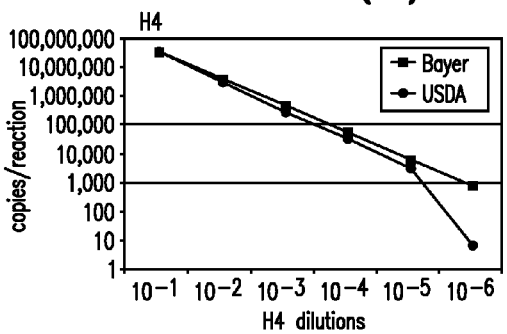
Figure 2E:
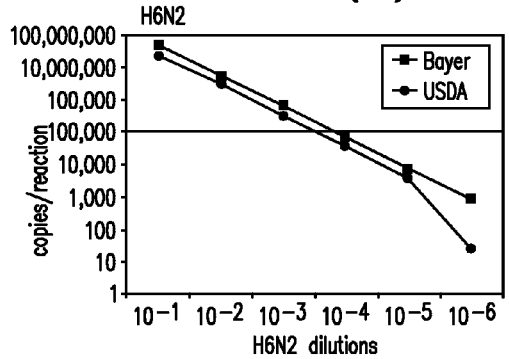
Figure 2F:
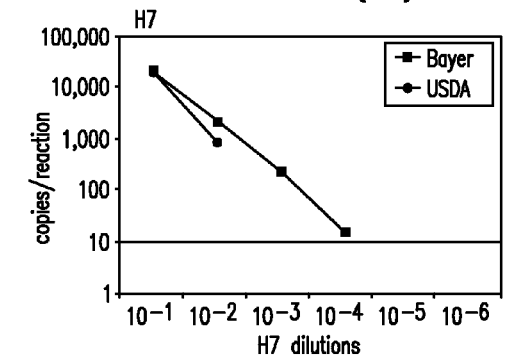
Figure 2G:
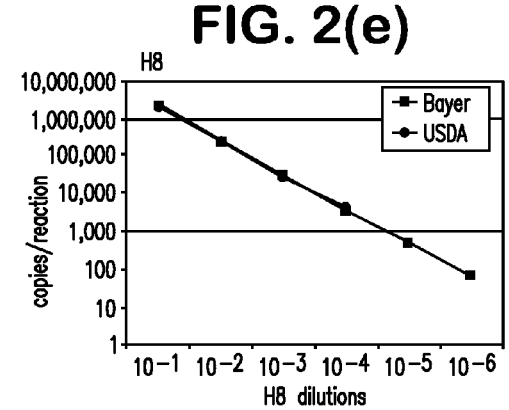
Figure 2H:
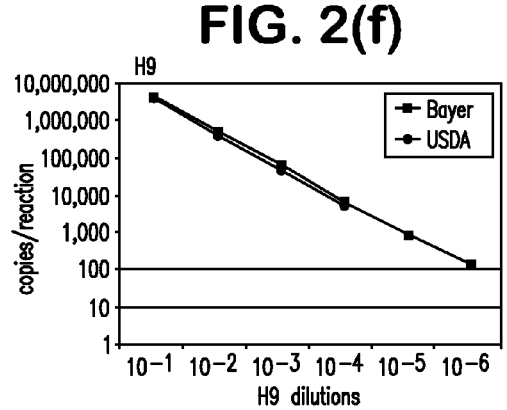

The term "consensus sequence" refers to a linear series of nucleotides, commonly with gaps and some degeneracy that define common features of homologous sequences. A consensus sequence is an idealized sequence in which each position represents the base (nucleotide) most often found when many actual sequences are compared.

The term "target" refers to the nucleic acid sequence of the influenza A virus.

The term "sample" refers to a biological sample from any subject that may be tested for the presence of one or more disease states, such as influenza virus or other respiratory disorders or diseases. Such samples may include tissue samples from skin or any organ, blood, plasma, mucus, saliva, etc.

The term "subject" refers to a biological organism from which a sample may be obtained. Within the context of the present invention, a subject will usually be a human patient; however, subject may also include any mammal, such as a pig, horse, or sea mammal, or a nonmammal, such as wild birds or domestic foul.

The term "amplification primer" refers to an oligonucleotide that is complementary to the cDNA or RNA target molecule and provides the 3'-OH-end of a substrate to which any DNA polymerase can add the nucleosides of a growing DNA chain in the 5' to 3' direction.

The term "probe" refers to an oligonucleotide capable of selectively hybridizing to the amplified target nucleic acid under appropriate conditions. The probe sequence is identified as being either a sense (i.e., complementary) sequence (+) or as an anti-sense (i.e., reverse complementary) sequence to the coding or sense strand (−). In a kinetic PCR format, the detection probes may consist of an oligonucleotide with a 5'-reporter dye (R) and a 3'-quencher dye (Q). A fluorescent reporter dye (i.e., FAM (6-carboxyfluoescenin), etc.) is typically located at the 3'-end. The detection probe acts as the TAQMAN® probe during the amplification and detection process.

As used herein, the term "nucleic acid" refers to polynucleotides such as deoxyribonucleic acid (DNA), and, where appropriate, ribonucleic acid (RNA). The term should also be understood to include, as equivalents, analogs of RNA or DNA made from nucleotide analogs, and, as applicable to the embodiment being described, single (sense or antisense) and double-stranded polynucleotides. Expressed Sequence Tags ("ESTs," i.e., small pieces of DNA sequence usually 200 to 500 nucleotides long generated by sequencing either one or both ends of an expressed gene), chromosomes, cDNAs, mRNAs, and rRNAs are representative examples of molecules that may be referred to as nucleic acids.

As used herein, the term "oligonucleotide" encompasses polydeoxyribonucleotides (containing 2-deoxy-D-ribose), polyribonucleotides (containing D-ribose), any other type of polynucleotide that is an N-glycoside of a purine or pyrimidine base, and other polymers containing nonnucleotidic backbones (e.g., protein nucleic acids and synthetic sequence-specific nucleic acid polymers commercially available from the Anti-Gene Development Group, Corvallis, Oreg., as NEUGENE™ polymers) or nonstandard linkages, providing that the polymers contain nucleobases in a configuration that allows for base pairing and base stacking, such as is found in DNA and RNA. Thus, "oligonucleotides" herein include double- and single-stranded DNA, as well as double- and single-stranded RNA and DNA:RNA hybrids, and also include known types of modified oligonucleotides, such as, for example, oligonucleotides wherein one or more of the naturally occurring nucleotides is substituted with an analog; oligonucleotides containing internucleotide modifications such as, for example, those with uncharged linkages (e.g., methyl phosphonates, phosphotriesters, phosphoramidates, carbamates, etc.), negatively charged linkages (e.g., phosphorothioates, phosphorodithioates, etc.), and positively charged linkages (e.g., aminoalkylphosphoramidates, aminoalkylphosphotriesters), those containing pendant moieties, such as, for example, proteins (including nucleases, toxins, antibodies, signal peptides, poly-L-lysine, etc.), those with intercalators (e.g., acridine, psoralen, etc.), those containing chelators (e.g., metals, radioactive metals, boron, oxidative metals, etc.), and those containing alkylators. There is no intended distinction in length between the terms "polynucleotide" and "oligonucleotide," and these terms will be used interchangeably. These terms refer only to the primary structure of the molecule. As used herein the symbols for nucleotides and polynucleotides are according to the IUPAC-IUBMB Joint Commission on Biochemical Nomenclature.

Oligonucleotides can be synthesized by known methods. Background references that relate generally to methods for synthesizing oligonucleotides include those related to 5'-to-3' syntheses based on the use of β-cyanoethyl phosphate protecting groups. See, e.g., de Napoli et al., Gazz Chim Ital 114:65 (1984); Rosenthal et al., Tetrahedron Lett 24:1691 (1983); Belagaje and Brush, Nuc Acids Res 10:6295 (1977); in references which describe solution-phase 5'-to-3' syntheses include Hayatsu and Khorana, J Am Chem Soc 89:3880 (1957); Gait and Sheppard, Nuc Acids Res 4: 1135 (1977); Cramer and Koster, Angew Chem Int Ed Engl 7:473 (1968); and Blackburn et al., J Chem Soc Part C, at 2438 (1967). Additionally, Matteucci and Caruthers, J Am Chem Soc 103: 3185-91 (1981) describes the use of phosphochloridites in the preparation of oligonucleotides; Beaucage and Caruthers, Tetrahedron Lett 22:1859-62 (1981), and U.S. Pat. No. 4,415,732 to Caruthers et al. describe the use of phosphoramidites for the preparation of oligonucleotides. Smith, Am Biotech Lab, pp. 15-24 (December 1983) describes automated solid-phase oligodeoxyribonucleotide synthesis; and T. Horn and M. S. Urdea, DNA 5:421-25 (1986) describe phosphorylation of solid-supported DNA fragments using bis(cyanoethoxy)-N,N-diisopropylaminophosphine. See also, references cited in Smith, supra; Warner et al., DNA 3:401-11 (1984); and T. Horn and M. S. Urdea, Tetrahedron Lett 27:4705-08 (1986).

The terms "nucleotide" and "nucleoside" refer to nucleosides and nucleotides containing not only the four natural DNA nucleotidic bases, i.e., the purine bases guanine (G) and adenine (A) and the pyrimidine bases cytosine (C) and thymine (T), but also the RNA purine base uracil (U), the non-natural nucleotide bases iso-G and iso-C, universal bases, degenerate bases, and other modified nucleotides and nucleosides. Degenerate bases consist of the doubly-degenerate pyrimidine derivative 6H,8H-3,4-dihydropyrimido[4,5-c][1, 2]oxazin-7-one (P), which when introduced into oligonucleotides base pairs with either G or A, and the doubly-degenerate purine derivative N6-methoxy-2,6-diaminopurine (K), which when introduced into oligonucleotides base pairs with either C or T. Universal bases are bases that exhibit the ability to replace any of the four normal bases without significantly affecting either melting behavior of the duplexes or the functional biochemical utility of the oligonucleotide. Examples of universal bases include 3-nitropyrrole and 4-, 5-, and 6-nitroindole, and 2-deoxyinosine (dI), that latter considered the only "natural" universal base. While dI can theoretically bind to all of the natural bases, it codes primarily as G.

Modifications to nucleotides and nucleosides include, but are not limited to, methylation or acylation of purine or pyrimidine moieties, substitution of a different heterocyclic ring structure for a pyrimidine ring or for one or both rings in the purine ring system, and protection of one or more functionalities, e.g., using a protecting group such as acetyl, difluoroacetyl, trifluoroacetyl, isobutyryl, benzoyl, and the like. Modified nucleosides and nucleotides also include modifications on the sugar moiety, e.g., wherein one or more of the hydroxyl groups are replaced with halide and/or hydrocarbyl substituents (typically aliphatic groups, in the latter case), or are functionalized as ethers, amines, or the like. Examples of modified nucleotides and nucleosides include, but are not limited to, 1-methyladenine, 2-methyladenine, $N^6$-methyladenine, $N^6$-isopentyl-adenine, 2-methylthio-$N^6$-isopentyladenine, N,N-dimethyladenine, 8-bromoadenine, 2-thiocytosine, 3-methylcytosine, 5-methylcytosine, 5-ethylcytosine, 4-acetylcytosine, 1-methylguanine, 2-methylguanine, 7-methylguanine, 2,2-dimethylguanine, 8-bromo-guanine, 8-chloroguanine, 8-aminoguanine, 8-methylguanine, 8-thioguanine, 5-fluoro-uracil, 5-bromouracil, 5-chlorouracil, 5-iodouracil, 5-ethyluracil, 5-propyluracil, 5-methoxyuracil, 5-hydroxymethyluracil, 5-(carboxyhydroxymethyl) uracil, 5-(methyl-aminomethyl)uracil, 5-(carboxymethylaminomethyl)-uracil, 2-thiouracil, 5-methyl-2-thiouracil, 5-(2-bromovinyl)uracil, uracil-5-oxyacetic acid, uracil-5-oxyacetic acid methyl ester, pseudouracil, 1-methylpseudouracil, queosine, inosine, 1-methylinosine, hypoxanthine, xanthine, 2-aminopurine, 6-hydroxyaminopurine, 6-thiopurine, and 2,6-diaminopurine.

The terms "complementary" and "substantially complementary" refer to base pairing between nucleotides or nucleic acids, such as, for instance, between the two strands of a double-stranded DNA molecule or between an oligonucleotide primer and a primer binding site on a single-stranded nucleic acid to be sequenced or amplified. Complementary nucleotides are, generally, A and T (or A and U), and G and C. Within the context of the present invention, it is to be understood that the specific sequence lengths listed are illustrative and not limiting and that sequences covering the same map positions, but having slightly fewer or greater numbers of bases are deemed to be equivalents of the sequences and fall within the scope of the invention, provided they will hybridize to the same positions on the target as the listed sequences. Because it is understood that nucleic acids do not require complete complementarity in order to hybridize, the probe and primer sequences disclosed herein may be modified to some extent without loss of utility as specific primers and probes. Generally, sequences having homology of 80% or more fall within the scope of the present invention. As is known in the art, hybridization of complementary and partially complementary nucleic acid sequences may be obtained by adjustment of the hybridization conditions to increase or decrease stringency, i.e., by adjustment of hybridization temperature or salt content of the buffer. Such minor modifications of the disclosed sequences and any necessary adjustments of hybridization conditions to maintain specificity require only routine experimentation and are within the ordinary skill in the art.

The term "hybridizing conditions" is intended to mean those conditions of time, temperature, and pH, and the necessary amounts and concentrations of reactants and reagents, sufficient to allow at least a portion of complementary sequences to anneal with each other. As is well known in the art, the time, temperature, and pH conditions required to accomplish hybridization depend on the size of the oligonucleotide probe or primer to be hybridized, the degree of complementarity between the oligonucleotide probe or primer and the target, and the presence of other materials in the hybridization reaction admixture. The actual conditions necessary for each hybridization step are well known in the art or can be determined without undue experimentation. Hybridization conditions also include a buffer that is compatible, i.e., chemically inert, with respect to primers, probes, and other components, yet still allows for hybridization between complementary base pairs, can be used. The selection of such buffers is within the knowledge of one of ordinary skill in the art.

It is understood by one of ordinary skill in the art that the isolation of DNA and RNA target sequences from a sample requires different hybridization conditions. For example, if the sample is initially disrupted in an alkaline buffer, double stranded DNA is denatured and RNA is destroyed. By contrast, if the sample is harvested in a neutral buffer with SDS and proteinase K, DNA remains double stranded and cannot hybridize with the primers and/or probes and the RNA is protected from degradation.

The terms "support" and "substrate" are used interchangeably to refer to any solid or semi-solid surface to which an oligonucleotide probe or primer, analyte molecule, or other chemical entity may be anchored. Suitable support materials include, but are not limited to, supports that are typically used for solid phase chemical synthesis such as polymeric materials and plastics for use in beads, sheets, and microtiter wells or plates examples including without limitation, polystyrene, polystyrene latex, polyvinyl chloride, polyvinylidene fluoride, polyvinyl acetate, polyvinyl pyrrolidone, polyacrylonitrile, polyacrylamide, polymethyl methacrylate, polytetrafluoroethylene, polyethylene, polypropylene, polycarbonate, and divinylbenzene styrene-based polymers; polymer gels; agaroses such as SEPHAROSE®; dextrans such as SEPHADEX®); celluloses such as nitrocellulose; cellulosic polymers; polysaccharides; silica and silica-based materials; glass (particularly controlled pore glass) and functionalized glasses; ceramics, and metals.

The term "label" as used herein refers to any atom or molecule that can be used to provide a detectable (preferably quantifiable) signal, and that can be attached to a nucleic acid or protein via a covalent bond or noncovalent interaction (e.g., through ionic or hydrogen bonding, or via immobilization, adsorption, or the like). Labels generally provide signals detectable by fluorescence, chemiluminescence, radioactivity, colorimetry, mass spectrometry, X-ray diffraction or absorption, magnetism, enzymatic activity, or the like. Examples of labels include fluorophores, chromophores, radioactive atoms (particularly $^{32}P$ and $^{125}I$), electron-dense reagents, enzymes, and ligands having specific binding partners. Enzymes are typically detected by their activity.

As used herein, the term "target amplification" refers to enzyme-mediated procedures that are capable of producing billions of copies of nucleic acid target. Examples of enzyme-mediated target amplification procedures known in the art include PCR, nucleic acid-sequence-based amplification ("NASBA"), transcription-mediated amplification ("TMA"), strand displacement amplification ("SDA"), and ligase chain reaction ("LCR").

The most widely used target amplification procedure is PCR, first described for the amplification of DNA by Mullins et al. in U.S. Pat. No. 4,683,195 and Mullis in U.S. Pat. No. 4,683,202. The PCR procedure is well known to those of ordinary skill in the art. In the PCR technique, a sample of DNA is mixed in a solution with a molar excess of two oligonucleotide primers of 10-30 base pairs each that are prepared to be complementary to the 3' end of each strand of the DNA duplex; a molar excess of unattached nucleotide bases (i.e., dNTPs); and DNA polymerase, (preferably Taq polymerase, which is stable to heat), which catalyzes the formation of DNA from the oligonucleotide primers and dNTPs. Of the two primers, one is a forward primer that will bind in the 5'-3' direction to the 3' end of one strand of the denatured DNA analyte and the other is a reverse primer that will bind in the 3'-5' direction to the 3' end of the other strand of the denatured DNA analyte. The solution is heated to 94-96° C. to denature the double-stranded DNA to single-stranded DNA. When the solution cools, the primers bind to the separated strands and the DNA polymerase catalyzes a new strand of analyte by joining the dNTPs to the primers. When the process is repeated and the extension products synthesized from the primers are separated from their complements, each extension product serves as a template for a complementary extension product synthesized from the other primer. In other words, an extension product synthesized from the forward primer, upon separation, would serve as a template for a complementary extension product synthesized from the reverse primer. Similarly, the extension product synthesized from the reverse primer, upon separation, would serve as a template for a complementary extension product synthesized from the forward primer. In this way, the region of DNA between the primers is selectively replicated with each repetition of the process. Since the sequence being amplified doubles after each cycle, a theoretical amplification of one billion copies may be attained after repeating the process for a few hours; accordingly, extremely small quantities of DNA may be amplified using PCR in a relatively short period of time.

The terms "amplification sequence," "amplification product," and "amplicon" are used interchangeably to refer to the single-stranded sequences that are the end product of a PCR.

Where the starting material for the PCR is RNA, complementary DNA ("cDNA") is made from RNA via reverse transcription. The resultant cDNA is then amplified using the PCR protocol described above. Reverse transcriptases are known to those of ordinary skill in the art as enzymes found in retroviruses that can synthesize complementary single strands of DNA from an RNA sequence, such as for example, an mRNA or an ssRNA sequence as a template. The enzymes are used in genetic engineering to produce specific cDNA molecules from purified preparations of RNA (i.e., mRNA or ssRNA for example). A PCR used to amplify RNA products is referred to as reverse transcriptase PCR or "RT-PCR."

The terms "kinetic PCR" (kPCR) or "kinetic RT-PCR" (kRT-PCR), which are also referred to as "real-time PCR" and "real-time RT-PCR," respectively, refer to the detection of PCR products via a fluorescent signal generated by the coupling of a fluorogenic dye molecule and a quencher moiety to the same or different oligonucleotide substrates. Examples of commonly used probes used in kPCR and kRT-PCR include the following probes: TAQMAN® probes, Molecular Beacons probes, SCORPION® probes, and SYBR® Green probes. Briefly, TAQMAN® probes, Molecular Beacons, and SCORPION® probes each have a fluorescent reporter dye (also called a "fluor") attached to the 5' end of the probes and a quencher moiety coupled to the 3' end of the probes. In the unhybridized state, the proximity of the fluor and the quench molecules prevents the detection of fluorescent signal from the probe; during PCR, when the polymerase replicates a template on which a probe is bound, the 5'-nuclease activity of the polymerase cleaves the probe thus, increasing fluorescence with each replication cycle. SYBR® Green probe binds double-stranded DNA and upon excitation emit light; thus as PCR product accumulates, fluorescence increases.

The term "singleplex" refers to a single assay that is not carried out simultaneously with any other assays. Singleplex assays include individual assays that are carried out sequentially.

The term "multiplex" refers to multiple assays that are carried out simultaneously, in which detection and analysis steps are generally performed in parallel. Within the context of the present invention, a multiplex assay will include the use of the primers and probes, alone or in combination with additional primers and probes to identify, for example, an influenza virus along with one or more additional viruses. It is understood that with in the context of the present invention, that primers and probes for internal controls and/or additional respiratory viruses may be used together with the INFA and INFA primers and probes in a single multiplex assay.

Following is a description of some preferred embodiments and examples of the claimed invention. Additional embodiments and modifications in the function, purpose, or structure of the disclosed embodiments are intended to be covered by the claims of this application.

The avian and human INFA and human INFB amplification primers and detection probes of the present invention are consensus sequences that are derived by aligning multiple sequences and where appropriate incorporating degenerate and/or universal probes into the sequence to account for the high degeneracy found among the INFA and INFB sequences.

Avian Influenza A Primer and Probe Sets

In one embodiment of the present invention, there is provided avian INFA amplification primers and detection probes that amplify and detect the H5 subtype of avian INFA. The H5 primers and probes were designed based upon alignment of 55 avian and human INFA H5 sequences (Table 1). The H5 subtypes were selected due to the ability of these the avian subtypes to jump species and infect humans without rearrangement in an intermediate host, such as a pig. The avian H5 primer and probe sets were designed to accommodate the high degeneracy found throughout the HA region by choosing the most highly conserved regions of the HA gene sequences and where appropriate, including degenerate and/or universal bases. The specificity of the H5 primers and probes of the present invention have high specificity and are capable of differentiating the H5 avian INFA HA subtypes from the remaining 16 avian INFA HA subtypes.

Human Influenza A Primer and Probe Sets:

In another embodiment of the present invention, there is provided human INFA amplification primers and detection probes that amplify and detect the M1 matrix gene sequence of human INFA. The INFA matrix primers and probes were designed based upon alignment of 414 human matrix protein gene sequences from 13 subtypes of human INFA. The human INFA primer and probe sets were designed to accommodate the high degeneracy found throughout the human INFA genome by choosing the most highly conserved regions of the matrix and where appropriate including degenerate and/or universal bases. By designing the primers and probes as such, the human INFA matrix primers and probes of the present invention are capable of detecting all of the known human INFA subtypes. By aligning the human INFA matrix sequences with the avian INFA matrix sequences, the human INFA primers and probes may be used to amplify and detect avian INFA as well.

Example 4 illustrates the use of the human INFA matrix primers and probes of the present invention in an INFA matrix assay using kRT-PCR to test tissue culture extracts for $H1N_1$ and H5N2. Because the INFA matrix assay may be used to detect and amplify all known human INFA subtypes, it is to be understood and appreciated that Example 4 is merely illustrative of the use of the INFA matrix assay to detect INFA subtypes and in no way limits the use of the assay for the detection of only the H1N1 and H5N2 subtypes. FIGS. 2(*a*) to 2(*h*) (Example 6) also illustrate the use of human INFA matrix primers and probes of the present invention for the detection of influenza subtypes H1, H3, H4, H6, H7, H8, and H9.

Human Influenza B Primer and Probe Sets:

In a further embodiment of the present invention, there is provided human INFB amplification primers and probes that amplify and detect the nonstructural genes (NS1 and NS2) of human INFB. The INFB structural gene primers and probes were designed based upon alignment of 117 human segment 8 (NS1 and NS2) gene sequences (Table 3). Like the avian and human INFA primers and probes described supra, the human INFB primer and probe sets were designed to accommodate the high degeneracy found throughout the INFB B genome by choosing the most highly conserved regions of the nonstructural gene sequences and where appropriate including degenerate and/or universal bases.

Uses

The primers and probes of the present invention are useful for diagnostic assays to determine if a subject, be it avian or human, is infected with a particular strain or subtype of INFA or INFB. Such assays include any nucleic acid amplification tests (NAATS) for use on clinical samples, which include without limitation NAATs such as PCR, RT-PCR, kPCR, kRT-PCR, southern blot analysis, and linear amplification. In a preferred embodiment of the present invention, the primers and probes are used in a kPCR assay for the detection of INFA and INFB in any human or animal subject.

The primers and probes of the present invention may be used in a singleplex assay to test a single sample for the detection of a single INFA or a single INFB (Example 4 shows the use of the primers and probes of the present invention in a singleplex assay to detect and quantify INFA) or they may be used in a multiplex assay to test a human sample for one or more INFA and INFB (Example 5, Table 7 shows the use of the primers and probes of the present invention in a multiplex format to detect and quantify INFA and INFA). The INFA and/or INFB primers and probes may also be used in a multiplex assay in combination with other amplification primers and detection probes for the simultaneous detection of the INFA and/or INFB along with other respiratory organisms, such as parainfluenza 1, 2, 3, and 4, RSV A and B, metapneumovirus, adenovirus, *Chlamydia pneumoniae*, *Mycoplasma pneumoniae*, and *Legionella pneumophdia* (Example 5, Table 8 shows the use of the primers and probes of the present invention in a multiplex format to detect and quantify INFA and INFB in a panel. The presence of additional viruses such as rhinovirus, paraflu, and respiratory syncytial virus ("RSV") did not effect the specificity of the primers and probes of the present invention The primers and probes of the present invention may also be included in a kit that is used by clinicians to detect human and avian influenza viruses in patients that are afflicted with influenza symptoms. Such kit will include one or more primer and probe sets for the detection of avian INFA, human INFA, or human INFB.

As previously noted, the primers and probes disclosed herein are illustrative of the primers and probes that may be designed in order to determine if a subject is infected with INFA or INFB; thus, in another embodiment of the present invention, there is provided a method for preparing primers and probes for the detection of influenza viruses comprising consensus sequences derived from multiple strains and subtypes of influenza and incorporating degenerate and/or universal bases into the sequences where appropriate.

It is to be understood that while the invention has been described in conjunction with the preferred specific embodiments thereof, that the foregoing description as well as the examples that follow are intended to illustrate and not limit the scope of the invention. Other aspects, advantages and modifications within the scope of the invention will be apparent to those skilled in the art to which the invention pertains.

All patents and publications mentioned herein are incorporated by reference in their entireties.

The following examples are put forth so as to provide those of ordinary skill in the art with a complete disclosure and description of how to make and use the compositions of the invention. The examples are intended as non-limiting examples of the invention.

EXPERIMENTAL

The practice of the present invention will use, unless otherwise indicated, conventional techniques of molecular biology, biochemistry, microbiology, and the like, which are within the skill of the art. Such techniques are explained fully in the literature. See, for example, Sambrook, et al., MOLECULAR CLONING: A LABORATORY MANUAL, $2^{nd}$ ed. (1989); OLIGONUCLEOTIDE SYNTHESIS (M. J. Gait, ed., 1984); THE PRACTICE OF PEPTIDE SYNTHESIS (M. Bodanszky and A. Bodanszky, $2^{nd}$ ed., Springer-Verlag, New York, N.Y., 1994); NUCLEIC ACID HYBRIDIZATION (B. D. Haines & S. J. Higgins, eds., 1984); and METHODS IN ENZYMOLOGY (Elsevier, Inc., Burlington, Mass.).

In the examples that follow, efforts have been made to ensure accuracy with respect to numbers (e.g., amounts, temperature, etc.), but experimental error and deviations should be taken into account when conducting the described experiments. Unless indicated otherwise, parts are parts by weight, temperature is degrees centigrade, pressure is at or near atmospheric, and all experimental ingredients were obtained from commercially available sources.

Sequences used to determine the consensus sequences of the primers and probes of the present invention were obtained from the Influenza Sequence Database. Macken et al., Options for the Control of Influenza IV, pp. 103-106 (A. D. M. E. Osterhaus, N. Cox & A. W. Hampson (eds.) Amsterdam: Elsevier Science, 2001). Vector NTI AlignX software (Invitrogen Corp., Carlsbad, Calif.) was used to align homologous sequences.

The following notation is used in the examples: "AV" stands for avian; "INFA" stands for influenza A; "INFB" stands for influenza B; "H5" stands for the H5 subtype of avian INFA; "M" stands for the matrix protein genes (M1 and M2); "Seg8" stands for the nonstructural protein genes (NS1 and NS2); "Fw" stands for forward primer; "Rv" stands for reverse primer; "P" stands for probe; "S" stands for sense strand; and "AS" stands for anti-sense strand; and "Ct" stands for cycle threshold (the cycle number at which significantly increased fluorescence is first detected above background).

The kRT-PCR assays used in the examples that follow were run on an MX3000P™ Real-Time PCR System (Stratagene, La Jolla, Calif.) with a run taking approximately 2.4 hours for up to 90 samples. Each kRT-PCR run contained a positive and a negative control as well as quantitation standards that consisted of serial dilutions of quantified INFA RNA viral culture extract. The standards were value assigned using quantified RNA transcripts generated from a cloned fragment from the tested region (e.g., the avian H5 region, the avian or human matrix gene region, or the human segment 8 region depending on what assay is being run). The value assigned viral extract standards were used to compare the cycle threshold (Ct) achieved for each of the assays. Each assay contained an internal control (IC) that was added to samples during extraction to assess the assay process for efficiency and presence of inhibitors. Specificity of the assays was confirmed by testing an INFA subtype panel, a panel of common human respiratory pathogens, and normal human respiratory tract tissues and fluids.

Example 1

Avian Influenza A H5 Subtype Amplification Primer and Detection Probe Sequences Table 1 identifies amplification primer and detection probe sets designed to amplify and detect the HA gene sequences of the H5 subtypes of avian INFA. Map location reference Accession No. AJ867074; sequence design based on alignment of 55 avian and human IFNA H5 sequences.

TABLE 1

| Seq. Name | Map Location | Sequences 5'-3' | Strand |
|---|---|---|---|
| AV INFA H5(EA)Fw 01 | 1505-1528 | CGTATGACTACCCGCAGTATTCAG (SEQ ID NO. 1) | (+) |
| AV INFA H5(EA)Rv 01 | 1665-1640 | CCATAARGATAGACCAGCTACCATGA (SEQ ID NO. 2) | (-) |
| AV INFA H5(A) Fw 01 | 1547-1568 | GGGAGGAAATAGACGGAGTCAA (SEQ ID NO. 3) | (+) |
| AV INFA H5(A)Rv 01 | 1684-1661 | ATGATCCATTAGAGCACATCCAAA (SEQ ID NO. 4) | (-) |
| AV INFA H5 P | 1612-1637 | R-ACAGTGGCGAGTTCCCTAGCACTGGC-Q (SEQ ID NO. 5) | (+) |

Example 2

Human Influenza A M1 Matrix Gene Amplification Primer and Detection Probe Sequences Table 2 identifies amplification primers and detection probes designed to amplify and detect the M1 gene sequences of human and avian INFA. Map location reference Accession No. AY340090; sequence design based on alignment of 414 avian and human INFA matrix sequences.

TABLE 2

| Seq. Name | Map Location | Sequences 5'-3' | Strand |
|---|---|---|---|
| INFA M1 S | 32-53 | CTTCTAACCGAGGTCGAAACGT (SEQ ID NO. 6) | (+) |
| INFA M1 AS | 233-215 | TGGGCACGGTGAGCGTGAA (SEQ ID NO. 7) | (-) |
| INFA M1 P | 71-91 | R-CCRTCAGGCCCCCTCAAAGCC-Q (SEQ ID NO. 8) | (+) |

Example 3

Human Influenza B Segment 8 Amplification Primer and Detection Probe Sequences Table 3 identifies amplification primers and detection probes designed to amplify and detect segment 8 (NS1 and NS2) gene sequences of human INFB. Map reference Accession No. AB120439; sequence design based on alignment of 117 human INFB NS1 and NS2 sequences.

TABLE 3

| Seq. Name | Map Location | Sequences 5'-3' | Strand |
|---|---|---|---|
| INFB NS S | 8-31 | ACAACATGACCACAACACAAATTG (SEQ ID NO. 9) | (+) |
| INFB NS AS | 89-67 | CACTCCARAATTCCTGCTTCAAA (SEQ ID NO. 10) | (-) |
| INFB NS P | 40-60 | R-CCRGGAGCAACCAATGC-CACC-Q (SEQ ID NO. 11) | (+) |

Example 4

INFA Singleplex Matrix Assay

The INFA matrix gene primers and probes of Example 2 were used in kRT-PCR assays to detect and amplify H1N1 and H5N2 from samples of viral RNA extract in a singleplex assay. The results of the INFA matrix assay for H1N1 is shown in Table 4 and the results of the INFA matrix assay for H5N5 is shown in Table 5. The results of the INFA matrix assays as shown in Tables 4 and 5 demonstrate that the primers and probes were successful at detecting and amplifying H1N1 and H5N2 from samples with very small copy numbers.

Table 6 outlines the precision and linearity calculations for the INFA matrix assay on samples having differing copy numbers. As shown in Table 6, the detection rate for samples having 100 or more copies of a particular INFA subtype is 100%. The detection profile for the INFA matrix assay is depicted graphically in FIG. 1.

TABLE 4

| | | | INFA matrix assay used to detect and amplify H1N1 | | | Internal Control | |
|---|---|---|---|---|---|---|---|
| | | Well | | | Quantity | | |
| Replicate | Dye | Type | Sample ID | Ct (dRn) | (copies) | Dye | Ct (dRn) |
| 1 | FAM | Standard | H1N1 $10^6$ Std | 21.54 | 1,000,000 | HEX | 30.41 |
| 2 | FAM | Standard | H1N1 $10^5$ Std | 24.83 | 100,000 | HEX | 30.78 |
| 3 | FAM | Standard | H1N1 $10^4$ Std | 28.13 | 10,000 | HEX | 30.75 |
| 4 | FAM | Standard | H1N1 $10^3$ Std | 31.37 | 1,000 | HEX | 31.10 |
| 5 | FAM | Standard | H1N1 $10^2$ Std | 34.64 | 100 | HEX | 31.00 |
| 6 | FAM | Standard | H1N1 $10^1$ Std | 37.34 | 10 | HEX | 31.36 |
| 7 | FAM | NTC | Negative Control | No Count | No Count | HEX | 30.92 |
| 8 | FAM | Unknown | H1N1 50 copy Positive Control | 35.64 | 42 | HEX | 31.31 |

TABLE 5

| | | | INFA matrix assay used to detect and amplify H5N2 | | | Internal Control | |
|---|---|---|---|---|---|---|---|
| | | Well | | | Quantity | | |
| Replicate | Dye | Type | Sample ID | Ct (dRn) | (copies) | Dye | Ct (dRn) |
| 19 | FAM | Standard | H5N2 $10^6$ Std | 21.60 | 1,000,000 | HEX | 30.33 |
| 20 | FAM | Standard | H5N2 $10^5$ Std | 25.06 | 100,000 | HEX | 30.60 |
| 21 | FAM | Standard | H5N2 $10^4$ Std | 28.21 | 10,000 | HEX | 30.84 |
| 22 | FAM | Standard | H5N2 $10^3$ Std | 31.73 | 1,000 | HEX | 31.31 |
| 23 | FAM | Standard | H5N2 $10^2$ Std | 34.67 | 100 | HEX | 31.32 |
| 24 | FAM | Standard | H5N2 $10^1$ Std | No Count | No Count | HEX | 30.59 |
| 25 | FAM | Unknown | Negative Control | No Count | No Count | HEX | 31.18 |
| 26 | FAM | Unknown | H5N2 50 copy Positive Control | 36.82 | 24 | HEX | 30.89 |

TABLE 6

| Concentration (copies/well) | % Detected | Log Difference from Linearity | Within-run % CV | Between-run % CV | Total % CV |
|---|---|---|---|---|---|
| 50 | 38.6% | −0.50 | 57.47 | 0 | 57.47 |
| 100 | 100.0% | 0.01 | 31.39 | 12.42 | 33.75 |
| 1000 | 100.0% | 0.02 | 17.07 | 9.26 | 19.42 |
| 10,000 | 100.0% | 0.01 | 11.34 | 4.57 | 12.23 |
| 100,000 | 100.0% | −0.01 | 9.82 | 5.18 | 11.11 |
| 1,000,000 | 100.0% | −0.03 | 11.64 | 6.04 | 13.12 |
| 10,000,000 | 100.0% | −0.06 | 15.89 | 7.19 | 17.45 |
| 100,000,000 | 100.0% | −0.15 | 13.67 | 7.46 | 15.57 |

Example 5

Multiplex Assay

Table 7 shows the results of a multiplex assay that screens for INFA and INFB and Table 8 shows the results of a multiplex assay that screens for INFA and INFB; Table 8 in particular shows that the presence of additional viruses, such as rhinovirus, paraflu, and RSV do not effect the specificity of the influenza primers and probes of the present invention. As previously noted, all assays are run concurrently with negative and positive controls.

TABLE 7

Screening for Influenza A and B in a INFA/INFB multiplex kRT-PCR Format with Influenza Primers and Probes

| Sample ID | FAM Threshold (dRn) | Ct (dRN) | INFA Quantity (copies) | Slope (dRn) | CY5 Threshold (dRn) | Ct (dRn) | INFB Quantity (copies) | Slope (dRn) | HEX Threshold (dRn) | IC Ct (dRN) |
|---|---|---|---|---|---|---|---|---|---|---|
| INFA $10^6$ | 0.1 | 21.66 | $10^6$ | −3.203 | 0.025 | No Ct | No Ct | −3.3 | 0.02 | 30.63 |
| INFA $10^5$ | 0.1 | 25.01 | $10^5$ | −3.203 | 0.025 | No Ct | No Ct | −3.3 | 0.02 | 30.51 |
| INFA | 0.1 | 28.22 | $10^4$ | −3.203 | 0.025 | No Ct | No Ct | −3.3 | 0.02 | 31.02 |

TABLE 7-continued

Screening for Influenza A and B in a INFA/INFB multiplex kRT-PCR Format with Influenza Primers and Probes

| Sample ID | FAM Threshold (dRn) | Ct (dRN) | INFA Quantity (copies) | Slope (dRn) | CY5 Threshold (dRn) | Ct (dRN) | INFB Quantity (copies) | Slope (dRn) | HEX Threshold (dRn) | IC Ct (dRN) |
|---|---|---|---|---|---|---|---|---|---|---|
| INFA $10^4$ | 0.1 | 31.70 | $10^3$ | −3.203 | 0.025 | No Ct | No Ct | −3.3 | 0.02 | 31.00 |
| INFA $10^3$ | 0.1 | 34.49 | $10^2$ | −3.203 | 0.025 | No Ct | No Ct | −3.3 | 0.02 | 31.00 |
| INFA $10^2$ | 0.1 | 37.66 | 10 | −3.203 | 0.025 | No Ct | No Ct | −3.3 | 0.02 | 31.21 |
| INFA $10^1$ | 0.1 | No Ct | No Ct | −3.203 | 0.025 | No Ct | No Ct | −3.3 | 0.02 | 31.05 |
| Neg | 0.1 | 35.68 | 46 | −3.203 | 0.025 | No Ct | No Ct | −3.3 | 0.02 | 31.24 |
| Pos 50 | 0.1 | No Ct | No Ct | −3.203 | 0.025 | 18.61 | $10^6$ | −3.3 | 0.02 | 31.11 |
| INFB $10^6$ | 0.1 | No Ct | No Ct | −3.203 | 0.025 | 22.30 | $10^5$ | −3.3 | 0.02 | 31.19 |
| INFB $10^5$ | 0.1 | No Ct | No Ct | −3.203 | 0.025 | 25.53 | $10^4$ | −3.3 | 0.02 | 31.21 |
| INFB $10^4$ | 0.1 | No Ct | No Ct | −3.203 | 0.025 | 28.79 | $10^3$ | −3.3 | 0.02 | 31.16 |
| INFB $10^3$ | 0.1 | No Ct | No Ct | −3.203 | 0.025 | 33.15 | $10^2$ | −3.3 | 0.02 | 30.64 |
| INFB $10^2$ | 0.1 | No Ct | No Ct | −3.203 | 0.025 | 34.87 | 10 | −3.3 | 0.02 | 30.98 |
| INFB $10^1$ | 0.1 | No Ct | No Ct | −3.203 | 0.025 | No Ct | No Ct | −3.3 | 0.02 | 31.51 |
| Neg | 0.1 | No Ct | No Ct | −3.203 | 0.025 | 33.20 | 45 | −3.3 | 0.02 | 30.91 |
| Pos 50 | | | | | | | | | | |

TABLE 8

Screening for INFA, INFB, Rhinovirus, Paraflu, and RSV in a multiplex kRT-PCR Format with Influenza Primers and Probes

| Sample ID | FAM Threshold (dRn) | Ct (dRN) | INFA Quantity (copies) | Slope (dRn) | CY5 Threshold (dRn) | Ct (dRN) | INFB Quantity (copies) | Slope (dRn) | HEX Threshold (dRn) | IC Ct (dRN) |
|---|---|---|---|---|---|---|---|---|---|---|
| Flu B1 neat | 0.1 | No Ct | No Ct | −3.203 | 0.025 | 24.16 | 25,000 | −3.3 | 0.02 | 31.34 |
| Flu B1 1:1000 | 0.1 | No Ct | No Ct | −3.203 | 0.025 | 33.40 | 39 | −3.3 | 0.02 | 31.13 |
| Flu A1 1:1000 | 0.1 | 33.65 | 198 | −3.203 | 0.025 | No Ct | No Ct | −3.3 | 0.02 | 30.78 |
| Flu A2 neat | 0.1 | 30.21 | 2,347 | −3.203 | 0.025 | No Ct | No Ct | −3.3 | 0.02 | 31.43 |
| Flu B1 1:10 | 0.1 | No Ct | No Ct | −3.203 | 0.025 | 27.45 | 2,508 | −3.3 | 0.02 | 30.90 |
| Flu A1 neat | 0.1 | 25.31 | 79,930 | −3.203 | 0.025 | No Ct | No Ct | −3.3 | 0.02 | 30.70 |
| Flu A2 1:100 | 0.1 | 36.59 | 24 | −3.203 | 0.025 | No Ct | No Ct | −3.3 | 0.02 | 30.53 |
| Flu A3 Neat | 0.1 | 20.26 | 3,002,000 | −3.203 | 0.025 | No Ct | No Ct | −3.3 | 0.02 | 30.60 |
| Flu B2 1:100 | 0.1 | No Ct | No Ct | −3.203 | 0.025 | 25.58 | 1,143 | −3.3 | 0.02 | 30.86 |
| Flu A3 1:1000 | 0.1 | 29.85 | 3,044 | −3.203 | 0.025 | No Ct | No Ct | −3.3 | 0.02 | 31.13 |
| Flu A4 neat | | 20.36 | 2,802,000 | −3.203 | 0.025 | No Ct | No Ct | −3.3 | 0.02 | 30.61 |
| Flu A4 1:100 | 0.1 | 27.16 | 21,070 | −3.203 | 0.025 | No Ct | No Ct | −3.3 | 0.02 | 30.90 |
| Flu A1 1:10 | 0.1 | 28.75 | 6,736 | −3.203 | 0.025 | No Ct | No Ct | −3.3 | 0.02 | 30.92 |
| Flu A + Rhino 1:10 | 0.1 | 28.56 | 7,725 | −3.203 | 0.025 | No Ct | No Ct | −3.3 | 0.02 | 30.96 |
| Flu A2 1:10 | 0.1 | 33.93 | 162 | −3.203 | 0.025 | No Ct | No Ct | −3.3 | 0.02 | 30.38 |

TABLE 8-continued

Screening for INFA, INFB, Rhinovirus, Paraflu, and RSV in a multiplex kRT-PCR Format with Influenza Primers and Probes

| Sample ID | FAM Threshold (dRn) | Ct (dRN) | INFA Quantity (copies) | Slope (dRn) | CY5 Threshold (dRn) | Ct (dRn) | INFB Quantity (copies) | Slope (dRn) | HEX Threshold (dRn) | IC Ct (dRN) |
|---|---|---|---|---|---|---|---|---|---|---|
| Flu A4 1:10 | 0.1 | 24.69 | 124,400 | −3.203 | 0.025 | No Ct | No Ct | −3.3 | 0.02 | 30.34 |
| Flu B1 1:100 | 0.1 | No Ct | No Ct | −3.203 | 0.025 | 30.48 | 303 | −3.3 | 0.02 | 30.88 |
| RSV 1:10 | 0.1 | No Ct | No Ct | −3.203 | 0.025 | No Ct | No Ct | −3.3 | 0.02 | 31.07 |
| Paraflu 1:10 | 0.1 | No Ct | No Ct | −3.203 | 0.025 | No Ct | No Ct | −3.3 | 0.02 | 31.24 |
| Flu A4 1:1000 | 0.1 | 30.07 | 2,598 | −3.203 | 0.025 | No Ct | No Ct | −3.3 | 0.02 | 31.11 |
| Flu B + Rhino 1:10 | 0.1 | No Ct | No Ct | −3.203 | 0.025 | 27.44 | 2,523 | −3.3 | 0.02 | 31.25 |
| Flu B2 1:10 | 0.1 | No Ct | No Ct | −3.203 | 0.025 | 25.23 | 11,810 | −3.3 | 0.02 | 30.96 |
| Flu A3 1:100 | 0.1 | 26.18 | 42,690 | −3.203 | 0.025 | No Ct | No Ct | −3.3 | 0.02 | 30.55 |
| Flu B2 1:1000 | 0.1 | No Ct | No Ct | −3.203 | 0.025 | 31.82 | 119 | −3.3 | 0.02 | 31.20 |
| Rhino 1:10 | 0.1 | No Ct | No Ct | −3.203 | 0.025 | No Ct | No Ct | −3.3 | 0.02 | 30.70 |
| Flu A3 1:10 | 0.1 | 24.65 | 128,200 | −3.203 | 0.025 | No Ct | No Ct | −3.3 | 0.02 | 30.70 |
| Flu B2 Neat | 0.1 | No Ct | No Ct | −3.203 | 0.025 | 21.56 | 153,300 | −3.3 | 0.02 | 30.59 |
| Negative | 0.1 | No Ct | No Ct | −3.203 | 0.025 | No Ct | No Ct | −3.3 | 0.02 | 30.53 |
| Flu A1 1:100 | 0.1 | 32.19 | 568 | −3.203 | 0.025 | No Ct | No Ct | −3.3 | 0.02 | 31.09 |
| Flu A2 1:1000 | 0.1 | No Ct | No Ct | −3.203 | 0.025 | No Ct | No Ct | −3.3 | 0.02 | 31.08 |

Example 6

Comparative Analysis of Avian INFA Assays on Viral Stocks

The INFA avian H5 and matrix assays of the present invention (Examples 1, 2, and 4) were compared against avian H5 and matrix assays standardized by the USDA-ARS. The INFA assays were conducted in two assay formats on the same set of avian viral stocks: (1) a pan-INFA assay format using a series of ten-fold dilutions of nucleic acid isolated from an INFA subtype panel that contained well-characterized viral isolates from hemagglutinin subtypes H1, H3, H4, H5, H6, H7, H8, and H9; and (2) an H5-specific assay format using quantified standards made from dilutions of viral extracts from an H5N2 isolate.

The INFA matrix and H5-specific assays of the present invention were conducted as described above in the discussion preceding Example 1. The pan-INFA matrix assay targeted an approximately 202 bp (base pair) region of the matrix gene and the H5-specific assay targeted an approximately 180 bp fragment from the hemagglutinin gene. As previously noted, the INFA matrix primers and probes of the present invention are designed to detect all currently known INFA subtype sequences.

The USDA-ARS INFA matrix and H5-specific assays were conducted using a one-step kRT-PCR assay on the following thermocyclers: a Bio-Rad Chromo4™ (Hercules, Calif.) for the INFA matrix assay and a Cepheid SMARTCYCLER® (Sunnyvale, Calif.) for the H5-specific assay (see, Spackman et al., J. CLIN. MICROBIOL. 40(9):3256-3260).

The lowest level of viral RNA detected (LoD) by the pan INFA matrix assays of the present invention and the USDA-ARS was determined by testing serial dilutions of high titer viral stocks from an INFA subtype panel that included the following members: H1, H3, H4, H5, H6, H7, H8, and H9. The relative sensitivity of the H5-avian INFA assays was determined by quantification of serial dilutions of high titer viral stocks from $1.6 \times 10^6$ to 30 copies of an H5N2 influenza isolate. The H5N2 standards were value assigned versus RNA transcripts from a cloned matrix fragment.

The results of the pan-INFA matrix assays are depicted graphically in FIGS. 2(a)-2(h) and the endpoint sensitivity results of each of the assay runs are set forth in Table 9 (the assays of the present invention are identified in the Figures as the "Bayer" assay; Bayer being the assignee of the present invention). FIGS. 2(a)-2(h) show the serial dilutions from which the data of Table 9 was acquired (FIG. 2(e) only shows one of the runs for the H6N2 subtype). Table 9 clearly shows that the INFA matrix assay of the present invention displayed greater sensitivity (i.e., lower LoD) than the USDA-ARS INFA matrix assay in eight of the ten assays performed; specifically, the H1N1, H3, H5N2, H7, H8, H9N2, and two of the three H6N2 assays. Overall, the pan-INFA matrix assay of the present invention had the lowest LoD throughout the dilution series of the subtype panel (1 to 3 ten-fold improvements). In addition, the quantitation of most of the subtypes was similar with the exception of the H1 subtype where the pan-INFA matrix assay of the present invention quantified the level of virus in the dilutions approximately 50 to 100 fold higher than the USDA-ARS pan-INFA matrix assay.

TABLE 9

| | Pan INFA Matrix Assay | | | | | | | | |
|---|---|---|---|---|---|---|---|---|---|
| | H1N1 | H3 | H4 | H5N2 | H6N2 | H6N2 | H6N2 | H7 | H8 | H9N2 |
| Present Invention | $10^{-5}$ | $10^{-6}$ | $10^{-6}$ | $10^{-4}$ | $10^{-6}$ | $10^{-6}$ | $10^{-6}$ | $10^{-4}$ | $10^{-6}$ | $10^{-6}$ |
| USDA-ARS | $10^{-2}$ | $10^{-4}$ | $10^{-6}$ | $10^{-3}$ | $10^{-5}$ | $10^{-6}$ | $10^{-5}$ | $10^{-2}$ | $10^{-4}$ | $10^{-4}$ |

Figure 3:
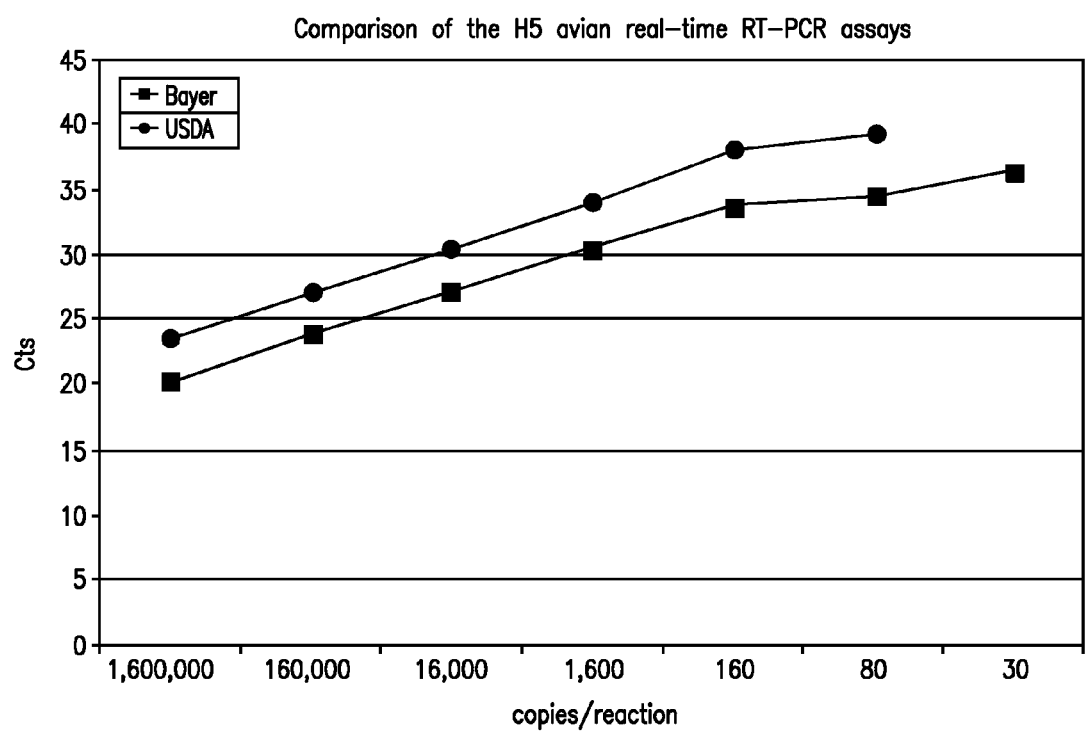
FIG. 3 shows the results of a comparative analysis of the same avian viral stock screened for the H5N2 subtype (American lineage) using the avian H5-specific assay of the present invention and the avian H5-specific assay used by the USDA-ARS.
Figure 4:
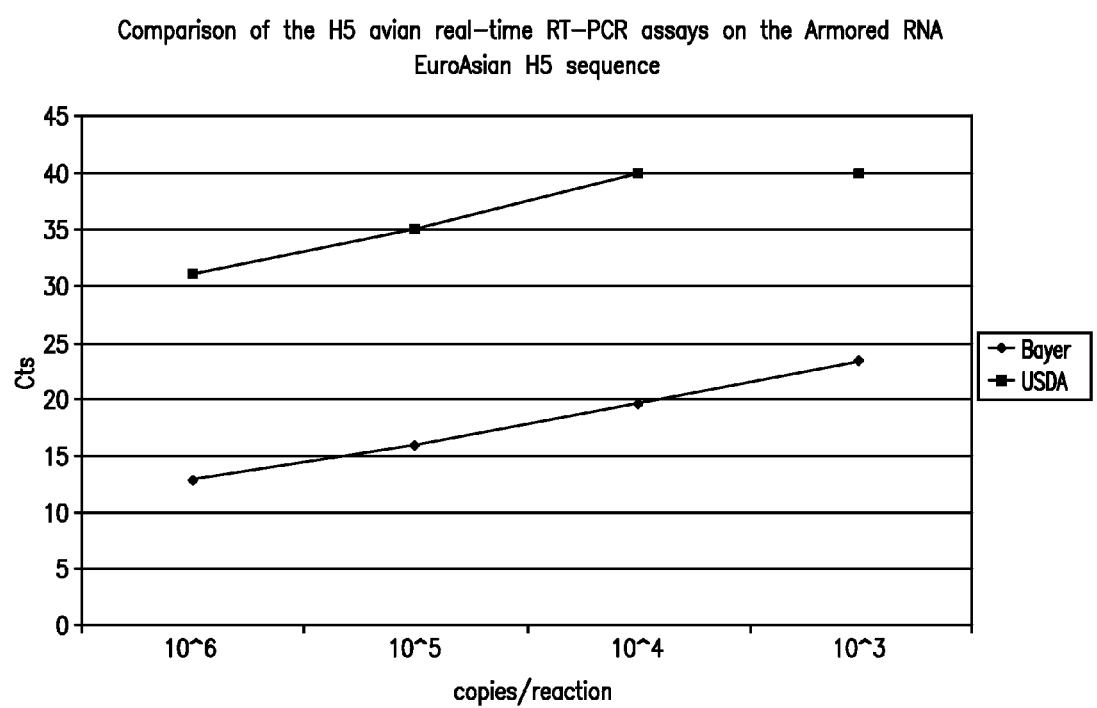
FIG. 4 shows the results of a comparative analysis of the same armored RNA (Eurasian lineage) using the avian H5-specific assay of the present invention and the avian H5-specific assay by the USDA-ARS.

The results of the H5-specific assays are shown in FIG. 3 and FIG. 4. FIG. 3 shows that while the H5-avian INFA assay of the present invention detected and quantified to 30 copies per reaction, the USDA-ARS H5-avian INFA assay quantified to 80 copies per reaction, indicating that the H5-avian INFA assay of the present invention is capable of detecting H5N2 (American lineage) at a lower Ct value than the H5-avian INFA assay of the USDA-ARS. FIG. 4 shows that when the H5-avian INFA assay and the USDA-ARS H5-avian INFA assay were compared on an armored RNA Eurasian-lineage sequence, the H5-avian INFA assay of the present invention detected the $10^4$ and $10^3$ copy dilution while the USDA-ARS H5 avian INF A assay did not detect these dilutions.

We claim:

1. A method of detecting and quantifying influenza viruses in a sample comprising conducting a kinetic polymerase chain reaction assay performed with primers and probes comprising SEQ ID NO. 1, SEQ ID NO. 2, SEQ ID NO. 3, SEQ ID NO. 4, SEQ ID NO. 5, SEQ ID NO. 6, SEQ ID NO. 7, SEQ ID NO. 8, SEQ ID NO. 9, SEQ ID NO. 10, and SEQ ID NO. 11.

2. A method of detecting and quantifying avian influenza virus A (INFA) in a sample comprising conducting a kinetic polymerase chain reaction assay performed with primers and probes comprising SEQ ID NO. 1, SEQ ID NO. 2, SEQ ID NO. 3, SEQ ID NO. 4, and SEQ ID NO. 5.

3. The method of claim 2, wherein the primers and probes detect and quantify subtype H5 of avian INFA.

4. A method of detecting and quantifying human influenza virus A (INFA) in a sample comprising conducting a kinetic polymerase chain reaction assay performed with primers and probes comprising SEQ ID NO. 6, SEQ ID NO. 7, and SEQ ID NO. 8.

5. The method of claim 4, wherein the primers and probes detect and quantify matrix genes of human INFA.

6. A method of detecting and quantifying human influenza virus B (INFB) in a sample comprising conducting a kinetic polymerase chain reaction assay performed with primers and probes SEQ ID NO. 9, SEQ ID NO. 10 and SEQ ID NO. 11.

7. The method of claim 6, wherein the primers and probes detect and quantify nonstructural genes of human INFB.

8. The method of claim 1, wherein the sample is a DNA sample obtained from a human or animal subject.

9. The method of claim 1, wherein the sample is an RNA sample obtained form a human or animal subject.

10. The method of claim 9, wherein the kPCR assay is a kinetic reverse transcriptase PCR (kRT-PCR) assay.

11. The method of claim 2 wherein the sample is a DNA sample obtained from a human or animal subject.

12. The method of claim 4 wherein the sample is a DNA sample obtained from a human or animal subject.

13. The method of claim 6 wherein the sample is a DNA sample obtained from a human or animal subject.

14. The method of claim 2 wherein the sample is a RNA sample obtained from a human or animal subject.

15. The method of claim 4 wherein the sample is a RNA sample obtained from a human or animal subject.

16. The method of claim 6 wherein the sample is a RNA sample obtained from a human or animal subject.

17. The method of claim 15, wherein the kPCR assay is a kinetic reverse transcriptase PCR (kRT-PCR) assay.

18. The method of claim 16, wherein the kPCR assay is a kinetic reverse transcriptase PCR (kRT-PCR) assay.

\* \* \* \* \*

SEQUENCE LISTING

<160> NUMBER OF SEQ ID NOS: 11

<210> SEQ ID NO 1
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 1
cgtatgacta cccgcagtat tcag                                              24

<210> SEQ ID NO 2
<211> LENGTH: 26
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 2
ccataargat agaccagcta ccatga                                            26

<210> SEQ ID NO 3
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 3
gggaggaaat agacggagtc aa                                                22

<210> SEQ ID NO 4
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 4
atgatccatt agagcacatc caaa                                              24

```
<210> SEQ ID NO 5
<211> LENGTH: 26
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 5
acagtggcga gttccctagc actggc                                              26

<210> SEQ ID NO 6
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 6
cttctaaccg aggtcgaaac gt                                                  22

<210> SEQ ID NO 7
<211> LENGTH: 19
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 7
tgggcacggt gagcgtgaa                                                      19

<210> SEQ ID NO 8
<211> LENGTH: 21
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 8
ccrtcaggcc ccctcaaagc c                                                   21

<210> SEQ ID NO 9
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 9
acaacatgac cacaacacaa attg                                                24

<210> SEQ ID NO 10
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 10
cactccaraa ttcctgcttc aaa                                                 23

<210> SEQ ID NO 11
```

-continued

```
<211> LENGTH: 21
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 11
ccrggagcaa ccaatgccac c                                               21
```